(12) United States Patent
Liljegren

(10) Patent No.: US 10,653,424 B2
(45) Date of Patent: May 19, 2020

(54) AIRWAY VALVE FOR IRREGULAR SHAPED AIRWAY

(71) Applicant: SPIRATION, INC., Redmond, WA (US)

(72) Inventor: Erik Liljegren, Redmond, WA (US)

(73) Assignee: SPIRATION, INC., Redmond, WA (US)

( * ) Notice: Subject to any disclaimer, the term of this patent is extended or adjusted under 35 U.S.C. 154(b) by 0 days.

(21) Appl. No.: 16/080,084

(22) PCT Filed: Jan. 31, 2017

(86) PCT No.: PCT/US2017/015746
§ 371 (c)(1),
(2) Date: Aug. 27, 2018

(87) PCT Pub. No.: WO2017/172024
PCT Pub. Date: Oct. 5, 2017

(65) Prior Publication Data
US 2019/0059906 A1 Feb. 28, 2019

Related U.S. Application Data

(60) Provisional application No. 62/315,250, filed on Mar. 30, 2016.

(51) Int. Cl.
*A61F 2/04* (2013.01)
*A61B 17/12* (2006.01)
*A61F 2/24* (2006.01)

(52) U.S. Cl.
CPC .. *A61B 17/12104* (2013.01); *A61B 17/12036* (2013.01); *A61B 17/12172* (2013.01);
(Continued)

(58) Field of Classification Search
CPC ................ A61F 2/20; A61F 2002/8043; A61F 2017/242
(Continued)

(56) References Cited

U.S. PATENT DOCUMENTS 6,929,637 B2 * 8/2005 Gonzalez ......... A61B 17/12022
604/11
7,011,094 B2 * 3/2006 Rapacki ........... A61B 17/12022
128/200.24
(Continued)

FOREIGN PATENT DOCUMENTS

JP 2005520631 A 7/2005
JP 2009532098 A 9/2009
(Continued)

OTHER PUBLICATIONS

AZOM Materials, Sep. 25, 2001.*
International Search Report, PCT/US2017/015746 (WO2017/172024A1) dated May 12, 2017.

*Primary Examiner* — Suzette J Gherbi
(74) *Attorney, Agent, or Firm* — Robert R. Richardson, P.S.

(57) ABSTRACT

A valve comprising: (a) a frame having: (i) a plurality of anchors and (ii) a plurality of struts; (b) a membrane connected to and spanning between each of the plurality of struts; wherein each of the plurality of struts have a free state and a loaded state and in the loaded state the membrane is substantially taut between two or more of the plurality of struts that are in the loaded state and in the free state the membrane is substantially taut between two or more of the plurality of struts that are in the loaded state.

15 Claims, 3 Drawing Sheets

(52) U.S. Cl.
CPC .......... *A61F 2/04* (2013.01); *A61B 17/12177* (2013.01); *A61F 2/24* (2013.01); *A61F 2002/043* (2013.01)

(58) Field of Classification Search
USPC ............................................................ 623/9
See application file for complete search history.

(56) References Cited

U.S. PATENT DOCUMENTS

| | | | | |
|---|---|---|---|---|
| 7,451,765 | B2* | 11/2008 | Adler | A61B 17/12104 128/200.26 |
| 7,691,151 | B2* | 4/2010 | Kutsko | A61B 17/12022 128/200.24 |
| 7,887,585 | B2* | 2/2011 | Gonzalez | A61B 17/12022 623/9 |
| 8,444,690 | B2* | 5/2013 | Gonzalez | A61B 17/12022 623/9 |
| 8,454,708 | B2* | 6/2013 | Kutsko | A61B 17/12022 128/200.24 |
| 8,647,392 | B2* | 2/2014 | Kutsko | A61B 17/12022 128/200.24 |
| 8,974,527 | B2* | 3/2015 | Gonzalez | A61B 17/12022 623/9 |
| 2003/0154988 | A1 | 8/2003 | DeVore et al. | |
| 2003/0158515 | A1 | 8/2003 | Gonzalez et al. | |
| 2005/0137714 | A1 | 6/2005 | Gonzalez et al. | |
| 2007/0232992 | A1* | 10/2007 | Kutsko | A61B 17/12022 604/30 |
| 2011/0098802 | A1* | 4/2011 | Braido et al. | A61F 2/82 623/2.19 |
| 2014/0371778 | A1 | 12/2014 | Rudakov et al. | |
| 2017/0181665 | A1* | 6/2017 | Johnson | A61B 5/1076 |
| 2019/0029691 | A1* | 1/2019 | Liljegren | A61B 17/12104 |

FOREIGN PATENT DOCUMENTS

| | | |
|---|---|---|
| JP | 2009534095 A | 9/2009 |
| WO | 2002094087 A1 | 11/2002 |

* cited by examiner

AIRWAY VALVE FOR IRREGULAR SHAPED AIRWAY

FIELD

The present teachings generally relate to a valve that has a pre-compressed state so that the valve can expand and seal airways that are irregularly shaped, and particularly the membrane remains taut and free of wrinkles in a fully expanded state or a partially expanded state so that the valve seals the irregularly shaped airway.

BACKGROUND

Mechanical airway valves are placed within a passageway to prevent air from flowing in selected portions of a lung.

It would be attractive to have a valve that can block an irregularly shaped passageway. What is needed is a valve that can expand in a major dimension and a minor dimension to mirror a shape of a passageway. It would be attractive to have a valve that has a membrane that is free of wrinkles when the struts are expanded outward, but are restricted from being fully expanded. What is needed is a valve that conforms to irregularly shaped passageways and seals the passageways.

SUMMARY

The present teachings meet one or more (if not all) of the present needs by providing a valve comprising: (a) a frame having: (i) a plurality of anchors and (ii) a plurality of struts; (b) a membrane connected to and spanning between each of the plurality of struts; wherein each of the plurality of struts have a free state and a loaded state and in the loaded state the membrane is substantially taut between two or more of the plurality of struts that are in the loaded state and in the free state the membrane is substantially taut between two or more of the plurality of struts that are in the loaded state.

The present teachings provide: a valve comprising: (a) a frame having: (i) a plurality of anchors and (ii) a plurality of struts; (b) a membrane connected to and spanning between each of the plurality of struts; wherein the membrane provides a load on each of the plurality of struts and the membrane is sufficiently elastomeric to (1) extend between each of the plurality of struts in a free state without the membrane wrinkling and (2) upon restriction of one or more of the plurality of struts, the membrane flexes into contact with a passageway so that the membrane substantially seals the passageway.

The teachings herein surprisingly solve one or more of these problems by providing a valve that can block an irregularly shaped passageway. The present teachings provide a valve that can expand in a major dimension and a minor dimension to mirror a shape of a passageway. The present teachings provide a valve that has a membrane that is free of wrinkles when the struts are expanded outward, but are restricted from being fully expanded. The present teachings provide a valve that conforms to irregularly shaped passageways and seals the passageways.

DETAILED DESCRIPTION

Figure 1:
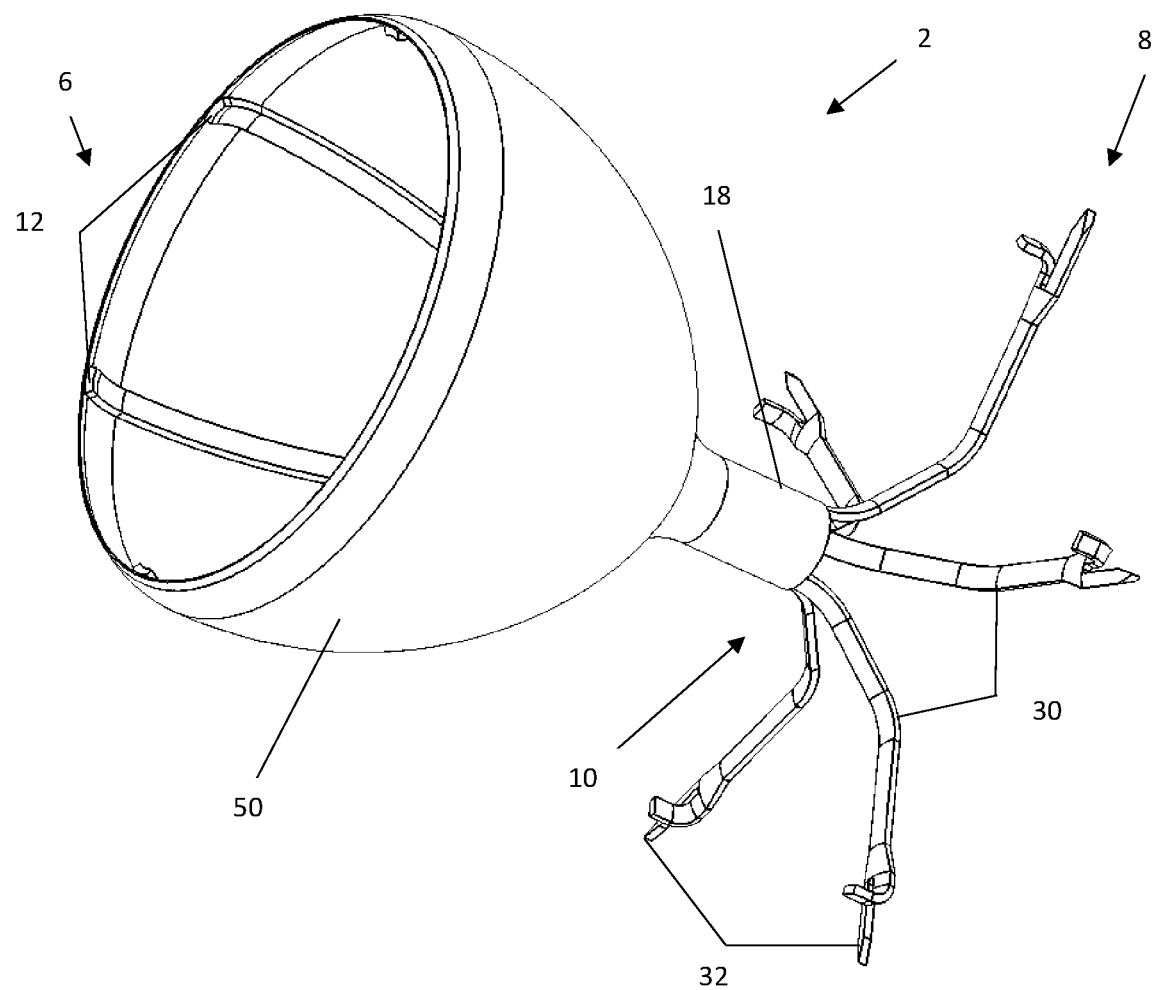
FIG. 1 illustrates a perspective view of a valve.

The explanations and illustrations presented herein are intended to acquaint others skilled in the art with the invention, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings provide an improved valve for placement in a passageway. The present teachings provide an improved airway valve. The valve functions to gradually open in an airway and block airflow through that airway. The valve may seal one or more structures such as passageways and preferably airways in a lung. Preferably, the valve forms a seal and prevents airflow in a bronchi, a bronchiole, a branch of a bronchi, a branch of a bronchiole, or a combination thereof. The valve may function to be removable. The valve may function to be biocompatible. The valve may extend along an axis. The valve may curve. The valve may be linear. The valve may bend in one or more locations, one or more directions, or both. The valve may bend and be rotatable. The valve may include one section. The valve may include a plurality of sections. The valve includes a distal end and a proximal end. The valve includes a longitudinal axis that extends from the distal end to the proximal end. The longitudinal axis may follow the shape of the valve such that the longitudinal axis is linear, arcuate, includes bends, or a combination thereof. Preferably, the longitudinal axis is a largest dimension of the valve and extends parallel to a length of the valve (e.g., a length).

The distal end may be the lead end and/or first end placed into an airway. The distal end may include a fixed anchor. The distal end may include a terminal point, be a terminal end, or both. The distal end may include one or more blunt features so that during deployment, the distal end contacts a wall of the airway and moves the airway while the airway remains intact. If more than one valve section is present then each valve section may include a distal end. The distal end may be located opposite the proximal end. One or more of the distal ends of a valve section may be in communication with a proximal end of an adjacent valve section.

The proximal end may be the last end to be deployed. The proximal end may include one or more retraction features. The proximal end may include one or more removal features. The proximal end may include a rod.

The rod may function as a support, a support for the frame, a central axis, or a combination thereof. The rod may be located in a center of the valve in the deployed state, the retracted state, or both. The rod may be located off center when the valve is in the deployed state, the retracted state, or both. For example, if 270 degrees of a passageway is substantially round and 90 degrees are oblong, the rod may be skewed towards the oblong portion so that the rod is not located in the center of the valve. The one or more rods may extend along a longitudinal axis of the valve, may be the longitudinal axis of the valve, or both. The rod may be used to remove the valve from a structure. The rod may release the connection with the walls of the passage and/or airway. The rod may move the struts so that the struts are relaxed from the deployed state or from being in contact with a wall of a passageway and the valve can be moved and/or removed. The distal end, the proximal end, or both may include one or more connection features, one or more removal features, one or more detachable features, or a combination thereof. The proximal end may include a bulbous portion, a hook, a hole, a "J" shape, or a combination thereof that assists in forming a connection so that the valve may be removed. The one or more rods may include one or more curves, one or more bends, or both. Preferably, the one or more rods may be generally straight (i.e., linear). The one or more rods may be hollow, solid, or both. The one or more rods may be flexible. The one or more rods may be made of nitinol, steel, surgical steel, stainless steel, plastic, a polymer, a thermoset, a thermoplastic, or a combination thereof. Preferably, the one or more rods and the struts are made of the same material. The one or more rods may be movable in one direction to assist in centering the valve within a passageway and especially a structure. The one or more rods may include through holes, dimples, indentations, recesses, raised sections, non-linear sections, or a combination thereof. The one or more rods may each include a distal end and a proximal end. The valve may include a plurality of rods that are connected together by one or more hinge points so that the valve may move through a non-linear path (e.g., a tortuous path).

The proximal ends may include one or more hinge points, one or more interconnects, or both. The valve may include more than one proximal end when the valve includes more than one valve section. The valve may include two or more sections and even a plurality of sections.

The valve section may include a frame that is covered by a membrane. The frame may function to move the membrane into contact with a passageway. The frame may function to secure the valve within a passageway. The frame may expand and contract. The frame may be the skeleton for the valve. The frame may provide longitudinal support for a membrane, radial support for the membrane, longitudinal support for the valve, or a combination thereof. The frame may be connected to a rod. The frame may move relative to the rod (e.g., expand radially away from the rod or move longitudinally relative to the rod). The frame may include one or more base members, one or more struts, one or more anchor connections, one or more anchors, or a combination thereof.

The base member may connect the struts, the anchors, or both to a rod. The base member and the struts, anchors, or both may be one integral piece. Each of the base members may function to axially move along a rod. The base members may function to axially restrict one end of a strut. The struts may be fixedly connected to the base member (e.g., welded, adhesively bonded, or both). The base member may be indirectly connected to the anchors by the struts. Each set of struts may include a base member. Two or more sets of struts may be connected to a single base member. The base member may lock to a rod. The base member may move along a rod. The base member may be movable to allow the struts to expand radially outward. Some base members may be axially movable, radially movable, or both and some base members may be static or immoveable. The base member may be welded to the rod, have a hole and pin configuration, crimped on the rod, adhered, soldered, or a combination thereof. The base members may be generally toroidally shaped, doughnut shaped, or both. The base members may be cylindrical. The base member may include a through hole that a rod extends through, and a set of struts may extend radially outward from the base member.

Each set of struts may function to work together to seal all or a portion of an airway (seal as discussed herein means prevent air from passing beyond the valve). Each set of struts may include three or more struts, four or more struts, five or more struts, preferably six or more struts, or even seven or more struts. The struts may be evenly distributed about the rod, the base member, or both. The struts may be asymmetrically distributed about the rod, the base member, or both. The set of struts is preferably one or more struts, and more preferably a plurality of struts. The one or more struts and preferably a plurality of struts may function to expand the membrane. For example, the struts may impart a force on the membrane so that the membrane is moved radially outward towards a wall of a passageway, and preferably into contact with the wall of the passageway. The one or more struts may function to move the membrane into contact with a structure (i.e., a passageway or an airway). Preferably, the one or more struts may function to move the membrane radially outward (e.g., towards a wall of a passageway). The struts may be movable so that expansion outward of the struts may vary from location to location to accommodate a size of a passageway. Each set of struts may exert a sufficient force on a passage or airway to form a seal with the passage or airway. Each strut may exert a sufficient force radially outward so that the strut expands a membrane, stretches a membrane, overcomes a force by a membrane, or a combination thereof. Each set of struts may exert a sufficient force so that a passage and/or airway is blocked by a membrane in communication with the struts. Each strut may exert an outward force of about 0.01 Kg or more, about 0.04 Kg or more, about 0.06 Kg or more, or even about 0.08 Kg or more. Each strut may exert a force of about 1 Kg or less, about 0.5 Kg or less, about 0.25 or less, or even about 0.1 Kg or less. The struts may function to expand so that the struts and membrane seal an airway, a passageway, or both. The struts may function to elastically deform from a closed position (i.e., a retracted state) to an open position (i.e., deployed state). Each of the struts may have a compressed state, a loaded state, and a free state.

The compressed state, loaded state, or both may be any state where an external force is acting on one or more of the struts such that the one or more struts are constrained (i.e., the struts are imparting a radial force outward but are prevented or restricted from expanding outward by an external force such as a membrane or a wall of a passageway). The compressed state may be a loaded state (i.e., a state where some load is acting upon the struts). The loaded state, preferably, is a state where the membrane is imparting a load or a force on one or more of the struts. One of the struts may be in a loaded state or compressed state. All of the struts may be in a loaded state or a compressed state. Some of the struts may be in a loaded state or a compressed state. Preferably, the loaded state may be a state where the membrane is applying some load on one or more of the struts such that one or more of the struts is prevented from expanding to a free state. The membrane may have an initial loaded state. The initial loaded state may be a state that occurs after the valve is formed, after the membrane is attached to the struts, or both. Once the struts begin to move for the first time the valve may no longer be in an initial loaded state and may move into a loaded state. The initial loaded state may be where the struts are compressed to a shape where the valve is loaded into a delivery device, a cartridge, or both for delivery to a location of interest. The initial loaded state may be a pre-loaded state where the membrane is connected to the struts so that when the struts are in a loaded state, a compressed state, or both the membrane is applying a load on the struts, the membrane is free of wrinkles, the membrane is taut, or a combination thereof. The initial loaded state may be where some load is acting upon the struts as soon as a connection is formed between the struts and the membrane and the struts are released to expand radially outward. The loaded sate may be pre-loaded state where a force is acting upon the struts before the struts are fully opened, in contact with a passage, or both so that the pre-load maintains the membrane in a wrinkle free state, taut, or both. The loaded state may apply a pre-load upon the struts so that the struts immediately upon being deployed and beginning to expand the membrane imparts tension upon the struts. The pre-load may be the membrane creating tension circumferentially on the struts (i.e., in a direction in line with the membrane), radially (i.e., a direction that imparts a force opposing radial expansion of the struts), or both. The pre-load may be the loaded state before one or more of the struts are fully expanded, at a deployed state, at a free state, in contact with a wall of a structure, or a combination thereof. The pre-load may be that the membrane elastically stretches with the struts as the struts expand outward so that the membrane imparts a load upon the struts throughout expansion of the struts into a fully expanded state. Preferably, the compressed state may be a state where a passageway, cartridge, valve delivery catheter, a passageway of an endoscope, bronchoscope, some device external to the valve, or a combination thereof are acting on the valve to compress one or more struts of the valve so that one or more of the struts are prevented from expanding to a free state. More preferably, the membrane reacts in the same way to both the compressed state and the loaded state and shrinks to remain substantially taut, wrinkle free, or both. The membrane may provide some load on the struts such that one or more of the struts cannot expand radially outward to a free state. More preferably, the membrane may provide a load on the struts so that all of the struts will not be in a free state at the same time. For example, if there are 6 struts on a valve then the membrane will restrict all 6 of the struts from expanding to a free state (i.e., the membrane will maintain a load on all of the struts). When one or more struts are in a loaded state one or more adjacent struts may be in a free state. When one or more struts are in a loaded state one or more adjacent struts may extend beyond a free state so that the valve mirrors the shape of the passageway. Preferably, when one strut is in a loaded state due to a passageway being non-circular (e.g., oval, have a flat wall, asymmetrical) one or more other struts are relieved of a load from the membrane and may expand outward into contact with the passageway so that the one more struts are in a free state or beyond a free state. A loaded state, a compressed state, or both may be any state where a strut is expanded a distance less than a free state.

The free state may function to be a state where no external forces are acting upon each of the struts, the membrane (i.e., the struts are not pulling the membrane radially outward), or both. Preferably, the free state is a state where the membrane is not applying a load upon a strut. The free state of the struts may be a state where one or more of the struts are fully expanded and there is no external force acting on the strut, which prevents the strut from continuing to expand outward. A free state may be a maximum expansion of a strut. A free state may be a maximum expansion of the struts when all of the struts are equally expanded outward. Preferably, the free state is where the membrane does not restrict the struts from expanding outward. For example, if no membrane is connected to the struts and no other forces are acting on the struts, the struts would expand to their free state. The free state may be where the struts are fully expanded a major distance (i.e., a cross-sectional length from the rod). The free state may be a state where some of the struts expand to a major distance. For example, when all of the struts are equally expanded outward (e.g., in a circular expansion) the struts may expand a distance X from the rod, which is less than the free state of all of the struts. However, if some of the struts are constrained by the membrane or a passage then some of the struts may expand a distance that is greater than a circular expansion distance (e.g., a distance X+1) and those struts may achieve a free state in the major distance. The membrane may be taut, free of wrinkles, or both in the free state.

The struts may extend from being located along the longitudinal axis to extending radially outward. The one or more struts may be formed into an open position and then closed until deployed where the struts elastically deform into the open position. Each of the plurality of struts may be individually movable. Each of the plurality of struts may move independent of the other struts. For example, one strut may be constrained and a second strut may move to a free state without effecting or being effected by a strut on either side. Each strut may individually move into contact with a wall so that the membrane extending between each of the struts may form a seal with the wall between the struts. The open position may be a free state, a compressed state, a loaded state, or a combination thereof. The open position may be where the struts are located a distance from the rod. Each strut may extend generally radially outward from a base member, a rod, or both. The struts may extend radially outward from the rod a distance (e.g., half of a cross-sectional distance (e.g., a radius)) of about 1 mm or more, about 2 mm or more, or about 3 mm or more. The struts may extend radially outward from the rod a distance of about 8 mm or less, about 6 mm or less, or about 4 mm or less. Each strut may form a "J" shape. Each strut may include one or more bends, two or more bends, or even three or more bends. Each strut may curve so that the strut extends radially outward from the base member. The strut as it extends outward from the base member may curve so that the angle relative to the base member extends away from the rod, the base member, or both and then parallel to the rod. Each strut in a fully relaxed state may have at least a section that is parallel with a base member, a rod, or both. The struts have a length. Each of the struts may have an identical length. Each strut may have a length of about 3 mm or more, about 4 mm or more, or even about 5 mm or more. Each strut may have a total length of about 10 mm or less, about 9 mm or less, or about 8 mm or less. Each strut may include one or more features for gripping tissue, a wall of a passage, a wall of an airway, or a combination thereof. Each strut may have a tip that curves inward, that extends towards the rod, or both. Preferably, the struts do not include a feature that penetrates a wall of a passage (e.g., tissue). The features that grip the passage may only do so by exerting a radially outward force. The struts may be made of any elastically deformable material. The struts may be made of a biocompatible material. The struts may be made of metal, plastic, a polymeric material, an alloy, or a combination thereof. Preferably, the struts may be made of nitinol (i.e., a nickel titanium alloy). Some struts may be directly connected to a rod and some struts may be connected to a base member and the struts may be connected to a membrane that extends between the struts and along the struts from the tip to the rod. The plurality of struts may be connected to a rod, a base member, an anchor or a combination thereof.

The one or more anchors may function to prevent movement of the valve when the valve is in the deployed state. The one or more anchors may function to prevent movement of one or more valve sections, one or more rods, the entire valve, or a combination thereof. The one or more anchors may function to prevent movement of the valve within a passage, an airway, or both so that the valve remains at a desired location. The one or more anchors may prevent axial movement of a valve section relative to a rod. The one or more anchors may be located at the distal end, the proximal end, or both ends of the valve. Preferably, the anchors extend from a central region of the valve (i.e., a location between the distal end and the proximal end). More preferably, the anchors extend from substantially the middle of the valve (i.e., within about 20 percent or less, about 15 percent or less, or about 10 percent or less of center). The one or more anchors may include one or more arms that attach the valve to a structure, prevent movement of the valve, or both.

The one or more arms may function to connect the valve to a structure. The one or more arms may function to prevent movement of the valve when the valve is deployed. The one or more arms may extend radially outward from a rod. The one or more arms may be made of nitinol, steel, surgical steel, stainless steel, plastic, a polymer, a thermoset, a thermoplastic, or a combination thereof. The one or more arms may include a first arcuate region, a second arcuate region, a third arcuate region, and an anchor tip. Each of the arcuate regions may be configured to extend from the rod and to angle the anchor tip so that the anchor tip connects the valve to a passageway, a structure, tissue, or a combination thereof.

The one or more anchor tips may function to grip a structure, pierce a structure, or both. The one or more anchor tips may pierce a structure (e.g., tissue of a structure) to anchor the valve. The one or more anchor tips may function to prevent the arms of the anchor form moving relative to a structure. The one or more anchor tips may extend into contact with and/or grip a structure, a passageway, tissue, or a combination thereof. The one or more anchor tips may have a tip that is pointed, blunt, rounded, flat, at an angle relative to the arms, or a combination thereof. The one or more anchor tips may extend outward beyond the main portion of the arms. The one or more anchor tips may be angled towards a distal end, a proximal end, or both. The anchor tips may extend at an angle of about 45 degrees or more, about 60 degrees or more, 75 degrees or more, or about 90 degrees or more from a main portion of the arm of the anchor, the arm to which the anchor tip is connected, or both. The anchor tips may be an anchor pad when the anchor tips extend at an angle of about 90 degrees with a main portion of the arm of the anchor. The anchor pads may restrict movement of the anchor tips towards the passageway, tissue, or both. The anchor pads may contact the tissue proximate to the anchor tips. The anchor pads may be an anchor tip that does not grip tissue or the passageway. The anchor tips may extend at an angle of about 150 degrees or less, about 135 degrees or less, about 115 degrees or less, or about 105 degrees or less relative to a main portion of the arm of the anchor, the arm to which the anchor tip is connected, or both. Some anchor tips may extend at an angle relative to the arms, and some anchor tips may extend coplanar with the arms. The anchor tips may have a length of about 1 mm or more, about 2 mm or more, or about 3 mm or more. The anchor tips may have a length of about 10 mm or less, about 8 mm or less, or about 5 mm or less. The anchor tip may hold the valve in place so that the membrane seals a passageway.

The membrane may function to prevent passage of fluids (e.g., air). The membrane may function to restrict airflow through a structure, a passageway, and preferably an airway. The membrane may be fluid impermeable. The membrane may be rigid. The membrane may be flexible. The membrane may be plastically deformable. Preferably, the membrane is elastically deformable. The membrane may be attached along a length of each strut. The membrane may extend around a circumference of the valve (i.e., from strut to strut around a circumference of the valve). Preferably, the membrane extends along a length of each of the struts and between each of the struts. The membrane may be attached at one or more points on each strut. The membrane may be attached to the struts along substantially an entire length of each strut (e.g., 70 percent or more, 80 percent or more, or even 90 percent or more of a length of a strut). The membrane may substantially surround all or a portion of a strut (i.e., from the rod to the tip of each strut). The membrane may be in communication with one set of struts. The membrane may be connected to and extend between each of the plurality of struts. The membrane may be connected to the struts when one or more of the struts are in an initial loaded state, compressed state, a free state, or a combination thereof. The material of the membrane may be sufficiently elastic that when the membrane is connected to the struts when the struts are in the free state, the membrane can be loaded or compressed and the material will remain elastically shrunk and remain taut between each of the plurality of struts such that the membrane is substantially free of wrinkles.

The membrane may be made of a material that has elasticity so that the membrane remains taut as the struts expand outward. For example, once deployed and the struts move from a compressed state towards a free state the membrane may be taught and free of wrinkles between the struts so that when the struts, membrane, or both move into contact with a wall of a passageway a seal is formed between the struts, membrane, or both and the wall so that fluids are substantially prevented from passing. The membrane may remain substantially taut in a compressed state, a loaded state, a free state, or a combination thereof. When the membrane is taut the membrane is substantially free of wrinkles (e.g., loose portions, portions that are not imparting any force on the struts, folded portions, non-linear segments, overlapping portions, or a combination thereof). When the membrane is free of wrinkles the membrane is generally linear so that the membrane is free of non-linear segments, overlapping portions, folded portions, loose portions, or a combination thereof. The membrane when taut may be imparting some force between two struts. The membrane when taut may be in tension between two struts. The membrane when taut may substantially mirror a shape of a passageway so that substantially no gaps are formed between the membrane and the wall of the passageway. Stated another way the struts move the membrane into contact with the walls of the passageway so that the valve is substantially free of gaps between the membrane and the wall of the passageway and the membrane substantially prevents passage of fluid between the membrane and the walls of the passage. The membrane may extend between the struts and mirror the shape of the passageway so that gaps, spaces, or both are not formed between the membrane and the passageway. The gaps, spaces, or both are an area where the membrane does not form a seal with a wall of a passageway and some fluid is permitted to pass between the membrane and the passageway. The membrane may be pliable so that the membrane may conform to the shape of the passageway and reduce the size of any gaps present, eliminate gaps, or both. The membrane may be pulled into contact with a passage, be retained in contact with a passage, or both by surface tension between the passage and the membrane. The membrane may move so that mucus or other material may pass by the membrane and then the membrane move back into contact with the passageway so that the gaps are eliminated. The valve may have about 6 gaps or less, about 5 gaps or less, about 4 gaps or less, preferably about 3 gaps or less, more preferably about 2 gaps or less, even more preferably about 1 gap or less, and most preferably about zero gaps. Preferably, about 1 gap or less exists between the membrane and the wall in a region between each pair of struts. More preferably, zero gaps exist between the membrane and the wall in a region between each pair of struts. The membrane may be made of a material that stretches with the struts so that as the membrane stretches gaps, spaces, or both are prevented and/or eliminated between the membrane and the wall of the passageway.

The membrane may function to prevent passage of fluids. The membrane may function to restrict airflow through a structure, a passageway, and preferably an airway. The membrane may be fluid impermeable. The membrane may be rigid. The membrane may be flexible. The membrane may be plastically deformable. Preferably, the membrane is elastically deformable. The membrane may be attached along a length of each strut. The membrane may be attached at one or more points on each strut. The membrane may substantially surround all or a portion of a strut (i.e., from the rod to the tip of each strut). The membrane may be in communication with one set of struts. The membrane may be made of a material that is stretchable from an initial loaded state through a loaded state or compressed state to a free state without wrinkling. The material may be stretchable so that the valve is configured to conform to a passageway having a diameter substantially the same size as the initial loaded state to the free state without wrinkles forming in the membrane. The membrane may be located on one set of struts and contacted by a second set of struts if the membrane is restricted so that the struts are not fully deployed (i.e., deployed to about 95 percent or less, about 90 percent or less, about 85 percent or less, or about 80 percent or less than full deployment). The membrane may be fully supported on one set of struts and then moved into contact with a structure to form a complete seal by a second set of struts moving the membrane into contact with the structure. Each set of struts may include a membrane. Each set of struts may individually move a membrane into contact with a surface so that each set of struts and respective membrane form a seal with the surface. The membrane may be made of a polyurethane, an aliphatic polycarbonate-based thermoplastic polyurethane, a polyethylene siloxane, a material that includes silicone, a silicone polyurethane, a fluoroelastomer, an acrylate polymer, a polyacrylate, or a combination thereof. The membrane may be made of a material with a modulus of elasticity of about 10 GPa or less, about 5 GPa or less, about 2 GPa or less, or even about 1 GPa or less. The material may have a modulus of elasticity of about 0.001 GPa or more, about 0.003 GPa or more, about 0.005 GPa or more, about 0.01 GPa or more, about 0.03 GPa or more, about 0.05 GPa or more, or even about 0.06 GPa or more.

The material of the membrane may have a modulus of elasticity of from about 0.00100 GPA to about 0.065 GPa. A material with a tensile stress at 100 percent strain of about 3 MPa or more, about 5 MPa or more, or more preferably about 8 MPa or more, about 12 MPa or more, about 15 MPa or more, or even about 20 MPa or more. The material may have a tensile stress at 100 percent strain of about 100 MPa or less, about 50 MPa or less, or about 30 MPa or less. A material with a tensile stress at 200 percent strain of about 4 MPa or more, about 7 MPa or more, about 10 MPa or more, about 15 MPa or more, or about 20 MPa or more. The material may have a tensile stress at 200 percent strain of about 100 MPa or less, about 50 MPa or less, or about 30 MPa or less. A material with a tensile stress at 300 percent strain of about 6 MPa or more, about 9 MPa or more, about 13 MPa or more, about 18 MPa or more, or about 20 MPa or more. The material may have a tensile stress at 300 percent strain of about 100 MPa or less, about 50 MPa or less, or about 30 MPa or less. A material with a tensile strength at break of about 15 MPa or more, about 20 MPa or more, or about 25 MPa or more (i.e., between about 15 MPa and about 30 MPa). The material may have a tear strength of about 40 kN/m or more, about 60 kN/m or more, about 75 kN/m or more, about 100 kN/m or more. The material may have a tear strength of about 200 kN/m or less, about 150 kN/m or less, or about 125 kN/m or less. When more than one membrane is used, one membrane may be elastic and one membrane may be non-flexible. For example, one membrane may be made of a thermoplastic polyurethane and one membrane may be made of a silicone polyurethane. The membrane may stretch without wrinkling. The membrane may be stretched by a force of the struts expanding from a retracted state to a deployed state. The membrane may be connected to a set of struts, a base member or both. The two or more struts and preferably a plurality of struts may be connected to a base member.

The deployed state may function to seal a passage, an airway, or both. The deployed state may function to extend the struts radially outward to support a valve substantially within a center of a passage and/or an airway. The deployed state may have the struts fully deployed and the movable anchors moved to a steady state (i.e., fully deployed location) where further movement of the valve does not occur. The deployed state may have the struts extending radially outward. The deployed state may be a compressed state, a loaded state, a free state, or a combination thereof. The fully deployed state may have the struts extending outward from the rod and into contact with a structure such as a passageway. The struts in the fully deployed state may have one or more struts that are in a compressed state, a loaded state, or both. The struts may be restricted from fully opening due to the structure such that a steady state or a free state is not achieved. The struts may gradually extend from the retracted state to the fully deployed state and may extend at an angle less than 90 degrees. The valve may slowly transition from a retracted state to a fully deployed state over time as the struts elastically deform back to a fully deployed state, as the struts stretch the membrane, or both. The struts, the anchors, or both may progressively open from the retracted state to the deployed state over a period of time (e.g., 6 hours or more, 12 hours or more, 24 hours or more, 1 day or more, 3 days or more, or even 1 week or more) so that a passage, airway, or both is progressively sealed as the struts fully open. The struts, the anchors, or both may rapidly open into contact with the structure such as a passageway (e.g., 5 minutes or less, 3 minutes or less, 1 minute or less, or even 30 seconds or less).

The retracted state may have the valve located within a capsule, a cartridge, a valve delivery catheter, a bronchoscope, or a combination thereof. The retracted state may have the struts, anchors, or both extending substantially parallel to the longitudinal axis. The retracted state may have the struts, anchors, or both pointing away from the distal end, towards, the proximal end, or both. The retracted state may have the struts, anchors, or both pointing in a direction so that during placement the struts do not inadvertently connect to any passages, walls, tissue, or a combination thereof. The retracted state may have the valve compacted so that the valve may travel through one or more passages, one or more air ways, a valve delivery catheter, a bronchoscope, or a combination thereof. The retracted state may allow the valve to travel through tortuous passages, airways, or both without connecting to the walls, tissue, or both. The retracted state may allow the valve to be placed in a second division, a third division, or even a fourth division of the airway tree. The retracted state may be ended once the valve is ejected from, released from, removed from, or a combination thereof a capsule, a cartridge, a valve delivery catheter, a bronchoscope, or a combination thereof.

The valve may be loaded into a cartridge so that the struts are maintained in a folded configuration, a parallel relationship to the longitudinal axis, or both. The valve may be ejected from the cartridge so that any pressure on the struts by the cartridge is released. The cartridge may be used to load the valve into a deployment device such as a valve delivery catheter, bronchoscope etc. The delivery catheter may be pulled backwards as the cartridge, valve, or both are released so that the valve is placed within a passage, an airway, or both. The delivery catheter may be pulled back so that the valve is maintained in a desired location, a predetermined location, at a collapsed location, or a combination thereof. Once the valve is deployed the struts may function to begin elastically deforming. The struts may be configured so that the struts seal a passage, an airway, or both as the struts elastically deform. The struts may be connected to the anchor and may form a connection with a passage, tissue, airway, a wall, or a combination thereof so that axial movement of the strut is substantially prevented.

FIG. 1 illustrates a valve 2. The valve 2 has a frame 10 that extends between a proximal end 6 and a distal end 8. The frame 10 has a plurality of struts 12 that are located at the proximal end 6 and the plurality of struts 12 are connected together by a membrane 50 that extends between each of the struts 12. The struts 12 are connected to anchors 30 by a base member 18. A plurality of anchors 30 are located at a distal end 8. Each of the plurality of anchors 30 include an anchor tip 32.

Figure 2:
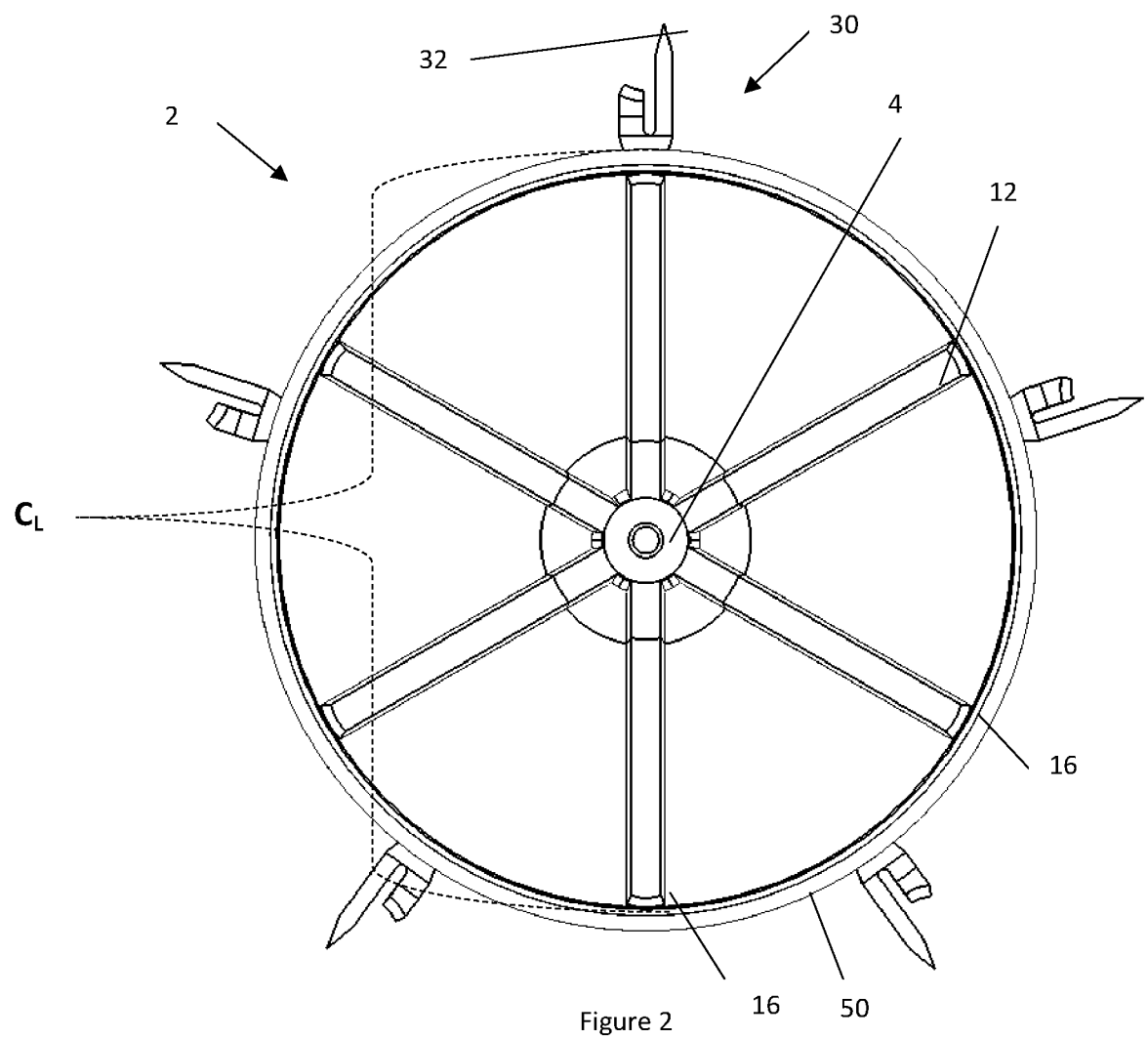
FIG. 2 illustrates a top view a valve.

FIG. 2 illustrates a top view of the valve 2. The valve 2 includes a rod 4 located substantially in a center of a plurality of struts 12. The plurality of struts 12 as shown are in a free state 16 where the struts are expanded out so that the valve is expanded to a maximum cross-sectional length ($C_L$) and the membrane 50 is substantially taught between each of the struts 12. An anchor 30 with anchor tips 32 expand outward beyond the membrane 50 so that the anchor 30 locks the valve 2 in place when the valve 2 is deployed.

Figure 3:
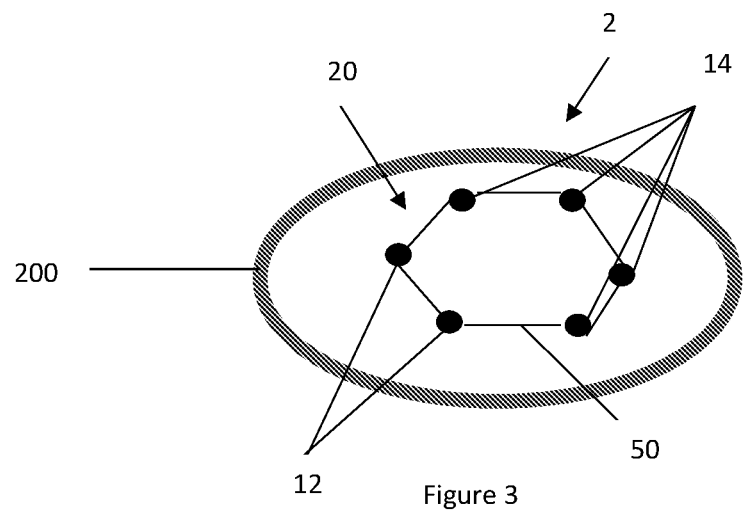
FIG. 3 illustrates a top view of pre-loaded valve being inserted into a passageway.

FIG. 3 illustrates a top view of a valve 2 during the initial stages of deployment into a passageway 200. The membrane 50 is extending between each of the plurality of struts 12 and the membrane 50 is in tension by the struts expanding outward, and the struts 12 are under tension by the membrane 50 pulling inward causing the valve to have a pre-load 20. Each of the struts 12 are shown in a compressed state 14 where the struts 12 have begun expanding outward, but the membrane 50 is restricting the movement of the struts outward.

Figure 4:
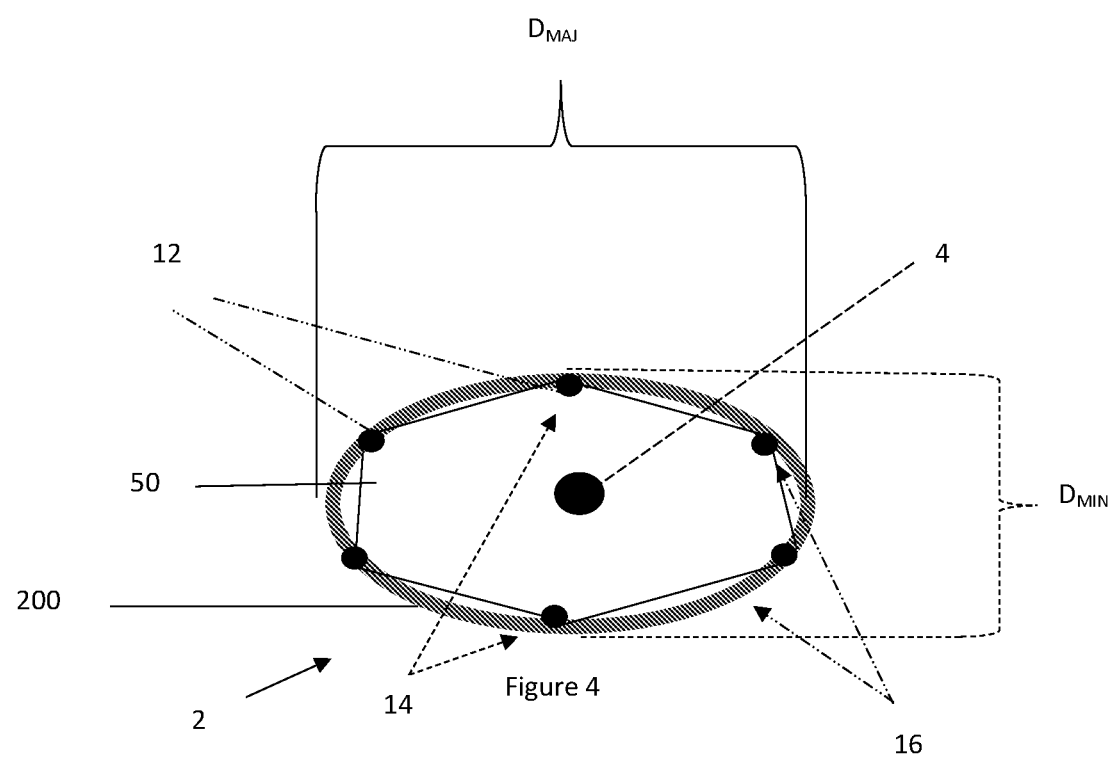
FIG. 4 illustrates a valve inserted into an irregularly shaped passageway.

FIG. 4 illustrates a valve 2 in a fully deployed state where the membrane 50 and struts 12 are moved into contact with a passageway 200. The passageway 200 as shown has a major cross-sectional length ($D_{MAJ}$) and a minor cross-sectional length ($D_{MIN}$). The struts 12 at the major cross-sectional length are in a free state 16 where the struts expand beyond a cross-sectional length when all of the struts 12 are fully expanded (as is shown in FIG. 2, for example). The struts 12 at the minor cross-sectional length are at a compressed state 14. The struts 12 in the compressed state 14 allow the struts 12 to move into a free state 16 to seal an irregularly shaped passageway 200.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

2 Valve
4 Rod
6 Proximal end
8 Distal end
10 Frame
12 struts
14 Compressed state
16 Free State
18 Base member
20 Preload
30 Anchor
32 Anchor tip
50 membrane
200 Passageway
$C_L$ Cross Sectional length
$D_{MAJ}$ Major Diameter
$D_{MIN}$ Minor Diameter

I claim:

1. A valve comprising:
   a. a frame having:
      i. a plurality of anchors and
      ii. a plurality of struts;
   b. a membrane connected to and spanning between each of the plurality of struts;
   wherein the membrane provides a load on each of the plurality of struts and the membrane is sufficiently elastomeric to (1) extend between each of the plurality of struts in a free state without the membrane wrinkling and (2) upon restriction of one or more of the plurality of struts from the free state to a loaded state, the membrane flexes into contact with a passageway so that the membrane substantially seals the passageway; and
   wherein the membrane has a modulus of elasticity of 0.1 GPa or less and 0.01 GPa or more,
   wherein the membrane is a silicone polyurethane.

2. The valve of claim 1, wherein each of the plurality of struts have a free state and in the free state the membrane is taught between each of the plurality of struts.

3. The valve of claim 1, wherein each of the plurality of struts provide a sufficient force to overcome the load of the membrane so that each of the plurality of struts expand outward to the free state while the membrane expands with each of the plurality of struts so that the membrane is free of wrinkles.

4. The valve of claim 1, wherein the membrane remains substantially taught when some of the plurality of struts are expanded to a free state in a major cross-sectional direction and some of the plurality of struts are expanded in a minor cross-sectional direction that is less than the major cross-sectional direction.

5. The valve of claim 4, wherein some of the struts expand a distance that is greater than the major cross-sectional direction.

6. A valve comprising:
   a. a frame having:
      i. a plurality of anchors and
      ii. a plurality of struts;
   b. a membrane connected to and spanning between each of the plurality of struts;
   wherein the membrane provides a load on each of the plurality of struts and the membrane is sufficiently elastomeric to (1) extend between each of the plurality of struts in a free state without the membrane wrinkling and (2) upon restriction of one or more of the plurality of struts from the free state to a loaded state, the membrane flexes into contact with a passageway so that the membrane substantially seals the passageway; and
   wherein the membrane has a modulus of elasticity of 0.1 GPa or less and 0.01 GPa or more,
   wherein some of the struts expand a distance that is greater than the major cross-sectional direction,
   wherein the membrane is a fluoroelastomer, an acrylate polymer or a polyacrylate.

7. A valve comprising:
   a. a frame having:
      i. a plurality of anchors and
      ii. a plurality of struts;
   b. a membrane connected to and spanning between each of the plurality of struts;
   wherein the membrane provides a load on each of the plurality of struts and the membrane is sufficiently elastomeric to (1) extend between each of the plurality of struts in a free state without the membrane wrinkling and (2) upon restriction of one or more of the plurality of struts from the free state to a loaded state, the membrane flexes into contact with a passageway so that the membrane substantially seals the passageway; and
   wherein the membrane has a modulus of elasticity of 0.1 GPa or less and 0.01 GPa or more, wherein the membrane is an aliphatic polycarbonate-based thermoplastic polyurethane or a polyethylene siloxane.

8. The valve of claim 6, wherein each of the plurality of struts have a free state and in the free state the membrane is taught between each of the plurality of struts.

9. The valve of claim 6, wherein each of the plurality of struts provide a sufficient force to overcome the load of the membrane so that each of the plurality of struts expand outward to the free state while the membrane expands with each of the plurality of struts so that the membrane is free of wrinkles.

10. The valve of claim 6, wherein the membrane remains substantially taught when some of the plurality of struts are expanded to a free state in a major cross-sectional direction and some of the plurality of struts are expanded in a minor cross-sectional direction that is less than the major cross-sectional direction.

11. The valve of claim 10, wherein some of the struts expand a distance that is greater than the major cross-sectional direction.

12. The valve of claim 7, wherein each of the plurality of struts have a free state and in the free state the membrane is taught between each of the plurality of struts.

13. The valve of claim 7, wherein each of the plurality of struts provide a sufficient force to overcome the load of the membrane so that each of the plurality of struts expand outward to the free state while the membrane expands with each of the plurality of struts so that the membrane is free of wrinkles.

14. The valve of claim 7, wherein the membrane remains substantially taught when some of the plurality of struts are expanded to a free state in a major cross-sectional direction and some of the plurality of struts are expanded in a minor cross-sectional direction that is less than the major cross-sectional direction.

15. The valve of claim 14, wherein some of the struts expand a distance that is greater than the major cross-sectional direction.

* * * * *